United States Patent [19]
Cooper

[11] Patent Number: 4,838,506
[45] Date of Patent: Jun. 13, 1989

[54] GUIDANCE DEVICE FOR ULTRASOUND GUIDED SURGICAL PROCEDURES

[76] Inventor: William I. Cooper, 300 N. 14th St., Easton, Pa. 18042

[21] Appl. No.: 206,796

[22] Filed: Jun. 15, 1988

[51] Int. Cl.⁴ ............................................. A61B 10/00
[52] U.S. Cl. .................................. 248/200; 248/251; 248/286; 248/309.1; 128/662.05
[58] Field of Search ............... 248/514, 122, 200, 251, 248/274, 286, 285, 287, 309.1, 316.1, 178; 128/662.05, 662.06

[56] References Cited

U.S. PATENT DOCUMENTS

| | | | |
|---|---|---|---|
| 908,751 | 1/1909 | Cooke | 248/286 |
| 2,445,009 | 7/1948 | Strauss | 248/200 |
| 3,827,686 | 8/1974 | Storkh | 248/286 |
| 4,108,165 | 8/1978 | Kopp | 128/662.05 |
| 4,608,989 | 9/1986 | Drue | 128/662.05 |
| 4,635,644 | 1/1987 | Yagata | 128/662.05 |
| 4,742,829 | 5/1988 | Law | 128/754 |

FOREIGN PATENT DOCUMENTS

| | | | |
|---|---|---|---|
| 25214 | 3/1981 | European Pat. Off. | 128/662.05 |
| 2942405 | 4/1981 | Fed. Rep. of Germany | 128/662.05 |
| 531992 | 8/1955 | Italy | 248/287 |
| 7513862 | 6/1976 | Netherlands | 128/662.05 |

Primary Examiner—Alvin C. Chin-Shue
Assistant Examiner—Robert A. Olson
Attorney, Agent, or Firm—Pollock, Vande Sande & Priddy

[57] ABSTRACT

A holder for a needle guide sleeve for use in cooperation with an ultrasonic probe. The holder comprises a base portion configured to engage the probe and an upwardly extending arm provided with a slot with which the needle guide sleeve rests. The needle guide sleeve within the slot is movable only in the two dimensions of the picture generated by the ultrasound probe, and can be inserted with or removed from the holder even when the transducer is in place with the human body.

6 Claims, 1 Drawing Sheet

GUIDANCE DEVICE FOR ULTRASOUND GUIDED SURGICAL PROCEDURES

FIELD OF THE INVENTION

This invention relates to ultrasound imaging systems and more particularly, to attachments for use with ultrasound probes to accurately guide a needle tip to a small target in a body.

BACKGROUND OF THE INVENTION

Sonography is becoming the technique of choice as a diagnostic aid in many surgical procedures since it does not involve any radiation danger to the patient, and it has become especially useful in obstetrical imaging and in treatment of human infertility by in-vitro fertilization and embryo transfer (IVF/ET). Diagnostic ultrasound has proved to be valuable for oocyte pickup in IVF/ET programs since ultrasound can guide a needle to a small target within the human body.

The original procedures using ultrasound in IVF/ET included abdominal imaging and puncturing; however, trans-abdominal scans limited image resolution because of the large distance from the target area to the probe. More recently, transvaginal imaging using a vaginal transducer and a transvaginal puncturing technique has been developed. This technique has been described in the paper by Wikland et al "Use of a Vaginal Transducer for Oocyte Retrieval in an IVF/ET Program", J. Clin. Ultrasound 15:245–251, May 1987, and in U.S. Pat. No. 4,742,829 to Law et al issued May 10, 1988, for "Intracavitary Ultrasound and Biopsy Probe for Transvaginal Imaging".

To improve the accuracy of puncturing in the target area, various devices have been designed to guide the needle into the selected body site. However, in general, these devices require that the needle assembly be mounted on the probe before insertion of the probe into the vagina. It is desirable to provide a needle guide holder for an ultrasound imaging system in which the needle guide can be placed on or removed from the probe while the transducer is still in the vagina so that the instruments can be placed in the urethra and vagina at separate times.

SUMMARY OF THE INVENTION

It is accordingly an object of this invention to provide an improved needle guide holder for ultrasound imaging systems.

It is another object of this invention to provide a needle guide sleeve holder especially useful in ultrasound-guided oocyte retrieval.

In accordance with this invention there is provided a holder for a needle guide sleeve for use in cooperation with the probe shaft of an intracavitary ultrasound probe. The holder comprises an elongated base portion and an upwardly extending arm secured to the base portion. The base portion is provided with a lower contact surface configured to extend along and engage the outer surface of the probe shaft, and the upwardly extending arm is provided with an open-ended slot for removably positioning the needle guide sleeve in the plane defined by the axes of the probe shaft and the elongated base portion.

This structure retains the needle guide sleeve and a needle inserted therein in the same two dimensional plane of the picture generated by the ultrasound transducer head, yet permits the needle guide sleeve to be inserted in or removed from the holder even when the transducer is in place in the human body.

DETAILED DESCRIPTION OF THE INVENTION

Figure 1:
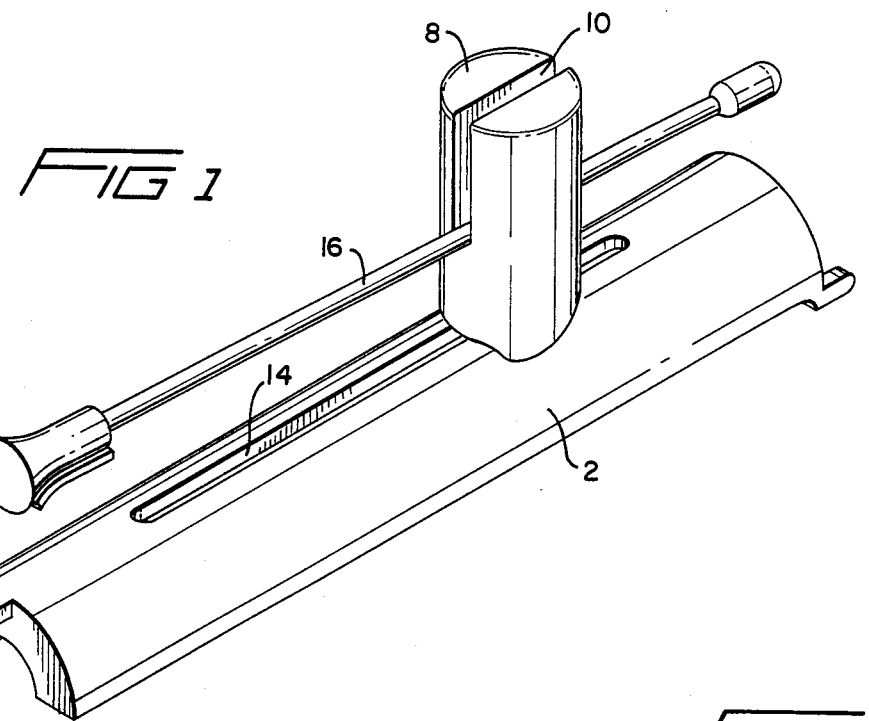
FIG. 1 is a perspective view of the holder for the needle guide sleeve.
Figure 2:
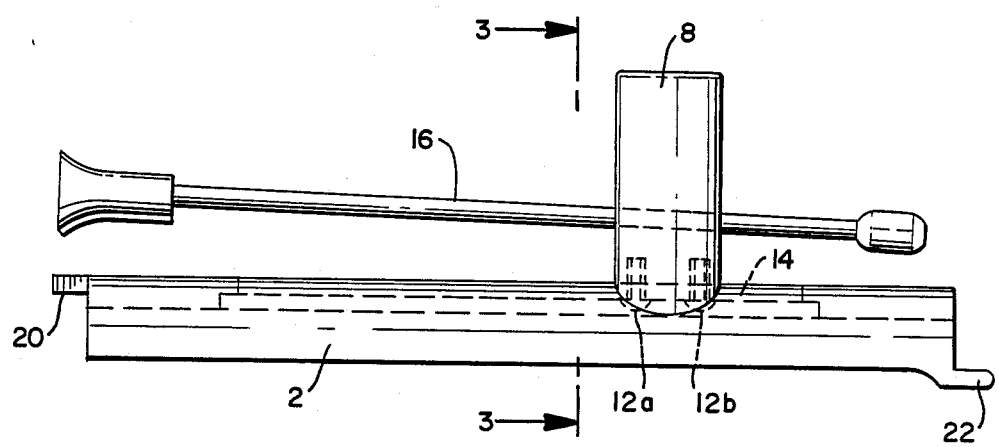
FIG. 2 is a side elevation view of the holder.
Figure 3:
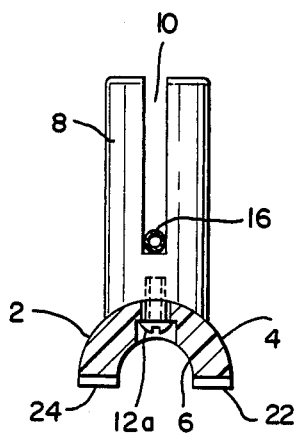
FIG. 3 is a front elevation view of the holder.

This invention is illustrated in detail by a holder which is specifically configured for use with the vaginal transducer of the General Electric 3000 intracavitary probe, which is described in detail in U.S. Pat. No. 4,742,829, issued May 10, 1988, to Law et al all details of which are hereby incorporated by reference. Although described in detail with respect to the Law et al probe, the configuration of the holder of this invention can readily be modified by workers skilled in the art to be used with other probe structures without departing from the invention.

As shown in the Figures, the holder comprises an elongated base 2 having an upper surface 4 and lower surface 6. Lower surface 6 is semicircular to fit the upper surface of the probe (not shown) which is circular in cross-section. Vertical arm 8 having slot 10 in the upper portion thereof is secured to base 2 by screws 12a, 12b and is adjustable longitudinally along groove 14 to allow for anatomical differences in the size of patients.

Projections 20, 22 and 24 at the ends of the base portion are sized to engage slots which are present in the GE 3000 intracavitary probe referred to herein.

Slot 10 in arm 8 holds needle guide sleeve 16 in the plane of the two-dimensional picture formed by the ultrasonic probe and is sized so that needle guide sleeve 16 fits snugly therein, permitting the needle guide sleeve to move in only two dimensions. The internal diameter of needle guide sleeve 16 is sized to accommodate the needle (not shown) which is to be used and minimize passage of fluid between the needle and the sleeve.

The holder described herein may be made of plastic or a metal such as stainless steel.

Having thus described the invention, the following Example is offered to illustrate it in more detail.

EXAMPLE

A holder which is configured to be used with the GE 3000 intracavitary probe was made in accordance with the Figures. The base was 14.7 cm long, had an outer diameter of 2.5 cm, an inner diameter of 1.2 cm. The vertical arm, having a diameter of 1.9 cm, extends 3.5 cm above the base and had a slot 0.4 cm wide and 2.4 cm. deep. The holder accommodated a needle guide which had a diameter of about 0.3 cm and an overall length of about 15 cm.

The foregoing description is intended to illustrate and not limit the invention, which may be readily modified by workers in the art to be useful with ultrasonic probes other than those described herein. For example, the upwardly extending arm need not be at right angles to the base, but can be inclined at an angle with respect to the base, and the base may be modified to conform to the shape of the probe with which it is to be used.

What is claimed is:

1. A guidance device for a needle guide sleeve, said device being adapted to fit securely onto the probe of an ultrasonic, intracavitary probe and comprising:
   (a) a rigid elongated base portion having a lower semicircular contact surface configured to extend along and engage an upper surface of said probe; and,
   (b) an upwardly extending arm secured to said elongated base portion, said arm having an axially-extending open-ended slot in the upper portion thereof, said slot being configured and oriented for removably positioning said needle guide sleeve in the two dimensions of the plane of the picture generated by said ultrasonic probe when it is in place withn the cavity being probed.

2. A guidance device for guiding a needle during use of said needle in an ultrasound surgical procedure, said device comprising:
   (a) a holder adapted to fit securely onto an intracavitary probe, said holder comprising a rigid elongated base portion having a lower contact surface configured to extend along and engage an upper surface of said probe, and an upwardly extending arm movably secured to said elongated base portion, said arm having an axially-extending open-ended slot in the upper portion thereof; and,
   (b) an elongated needle guide sleeve disposed in said open-ended slot, said guide sleeve being adapted to accommodate said needle, and said slot being configured and oriented for removably positioning said needle guide sleeve in the two dimensions of the plane of the picture generated by said ultrasonic probe when it is in place within a cavity being probed.

3. A guidance device in accordance with claim 2 wherein said base portion of said holder is provided with a longitudinally extending groove and means are provided for adjustably securing said upwardly extending arm to said base portion in a plurality of different positions along substantially the entire length of said groove.

4. A holder in accordance with claim 2 wherein said upwardly extending arm is disposed at substantially a right angle to said base portion.

5. The guidance device of claim 2 wherein said elongated base portion of said holder is provided with projections at the ends thereof for engaging said probe.

6. The guidance device of claim 2 wherein said lower contact surface of said base portion is substantially semicircular in cross-section.

* * * * *